United States Patent [19]

Stock et al.

[11] 4,294,997

[45] Oct. 13, 1981

[54] PROCESS FOR THE CONTROL OF PH IN THE ETHYNYLATION OF FORMALDEHYDE

[75] Inventors: Albert M. Stock, LaPorte; James D. Verbsky, Seabrook, both of Tex.

[73] Assignee: E. I. Du Pont de Nemours and Company, Wilmington, Del.

[21] Appl. No.: 923,371

[22] Filed: Jul. 10, 1978

[51] Int. Cl.$^3$ ........................................... C07C 33/046
[52] U.S. Cl. .................................................... 568/855
[58] Field of Search ........................................ 568/855

[56] References Cited

U.S. PATENT DOCUMENTS 3,957,888  5/1976  Reiss et al. ......................... 568/855
4,067,914  1/1978  Reiss et al. ......................... 568/855

Primary Examiner—Joseph E. Evans

[57] ABSTRACT

In the ethynylation of formaldehyde in the presence of a copper acetylide catalyst to produce butynediol, pH is controlled by the incremental or continuous addition of an alkali metal hydroxide and an alkali metal carbonate at an equivalent ratio of hydroxide ion to carbonate ion of 1:1–4:1.

14 Claims, No Drawings

PROCESS FOR THE CONTROL OF PH IN THE ETHYNYLATION OF FORMALDEHYDE

DESCRIPTION

1. Technical Field

This invention relates to an improved process for the preparation of butynediol by the reaction of acetylene and formaldehyde. More specifically, this invention relates to an improved process for the preparation of butynediol by the reaction of acetylene and formaldehyde in the liquid phase in the presence of an insoluble particulate copper complex catalyst and an alkali metal hydroxide and an alkali metal carbonate.

2. Background Art

The preparation of butynediol by the reaction of formaldehyde and acetylene in the presence of a slurry of copper acetylide catalyst is described in U.S. Pat. No. 3,154,589. An improved catayst and process for the production of butynediol is described by Kirchner in U.S. Patent Nos. 3,650,985 and 3,560,576. In the Kirchner patents it is disclosed that the pH of the reaction mixture during the ethynylation reaction may be maintained by removal of byproduct formic acid by ion exchange or acid acceptor treatment of the feed.

Calcium carbonate is disclosed as an acid acceptor. However, calcium carbonate has several disadvantages as an acid acceptor. First, due to its limited solubility, a large excess of finely divided calcium carbonate is generally required to maintain the preferred pH. Second, calcium carbonate, like all other basic calcium compounds, reacts with formic acid to produce calcium formate, which in the subsequent processing of crude filtrate from the butynediol reactor involving the stripping of formaldehyde and the hydrogenation of the residue directly over an activated nickel aluminum alloy catalyst to form an aqueous solution of butanediol, decomposes to insoluble calcium salts (e.g., calcium oxalate) which foul heat exchanger surfaces and produce deposits on the hydrogenation catalyst causing a loss in activity. Third, calcium carbonate has the disadvantage common to other carbonates, discussed in the following paragraph. Thus, there is a need to avoid the use of calcium carbonate and other calcium salts to control pH in such reactions.

Alkali metal carbonates and bicarbonates have also been disclosed as reagents for controlling pH in ethynylation reactions, for example, by U.S. Pat. No. 2,238,471 and by Alien Property Custodian, Ser. No. 327,820. Use of a mixture of carbonates and bicarbonates is disclosed by U.S. Patent 4,085,151. The major disadvantage of carbonate or bicarbonate salts, or mixtures thereof, is that, in reacting with formic acid, they generate so much carbon dioxide that the recycle acetylene is significantly diluted thereby. A substantial purge of the recycle gas is required to maintain acetylene concentration, which results in substantial acetylene losses. Thus, there is a need to at least minimize the use of bicarbonates or carbonates to minimize acetylene losses.

Control of pH during the ethynylation by adding sodium hydroxide is disclosed in British Pat. No. 1,455,761. Sodium hydroxide releases no carbon dioxide in the neutralization of formic acid, but controlling pH in ethynylation with strong bases such as sodium hydroxide is difficult at best. Zak (U.S. Pat. No. 4,085,151) has circumvented this difficulty by scrubbing $CO_2$ from the recycle gas with a solution of $Na_2CO_3$ and/or $NaHCO_3$, returning a portion of the $Na_2CO_3/NaHCO_3$ mixture to the reactor as buffer, and regenerzating the balance by adding NaOH. In effect, this process carries out the neutralization outside the reactor where careful control of pH is not so critical. The major disadvantage is that it requires substantial investment for process equipment which is avoided by the present invention. Use of the more weakly basic hydroxides $Mg(OH)_2$ or $Ca(OH)_2$ introduces $Ca^{++}$ or $Mg^{++}$ ions which foul catalysts used subsequently in hydrogenating the ethynylation product. $NH_4OH$ and/or $NH_3$ cannot be used since they will react with formaldehyde and interfere with the ethynylation reaction itself.

DISCLOSURE OF THE INVENTION

It has now been discovered that the preparation of butynediol by a process comprising contacting acetylene and formaldehyde in the presence of a copper acetylide catalyst in an agitated aqueous medium in a continuous reaction at about 60°–120° C. is improved by controlling the pH of the reaction mixture at from 5–8 by the incremental or continuous addition of an aqueous solution of an alkali metal hydroxide and an alkali metal carbonate added separately or as a mixture, so that a controlled quantity of $CO_2$ is maintained in the gas phase over the reaction mixture. It has been discovered that the presence of this controlled amount of $CO_2$ is a key ingredient in good pH control, since it moderates the effect of strongly basic reagents such as the alkali metal hydroxides.

The aforesaid alkali metal hydroxide/alkali metal carbonate is uniquely suitable as a pH control agent, since it provides the desired amount of $CO_2$ (3–9% by volume of the noncondensable gases) and at the same time avoids the generation of excessive carbon dioxide, which would require a purge rate higher than that needed to control other impurities present in the acetylene feed. It also avoids the significant investment for equipment required by the scrubbing scheme proposed by Zak (U.S. Pat. No. 4,085,151). Insoluble salt formation and/or fouling of catalyst and equipment used in related processes is also minimized with the avoidance of undesirable calcium salts.

The aqueous solution of the carbonate and the hydroxide is conveniently added directly to the ethynylation reaction or to the aqueous formaldehyde fed to the ethynylation reaction in amounts necessary to maintain the reaction mixture at the desired pH. The pH may be monitored within the reactor or in the liquid effluent stream from the reactor. Generally, the pH is maintained between 5 and 8. Preferably, the pH is maintained in the range of 6–6.5.

The aqueous solution of the carbonate and the hydroxide is preferably added as a mixture.

The carbonate and hydroxide solution may be added incrementally or continuously to avoid an excess being present at any one time. Thus, the solution should be added at a rate such that the concentration of free soluble alkali is not in excess of that required to obtain the desired pH for the reaction. The presence of an excess can cause the formation of undesirable byproducts by side reactions and it can also cause excess usage of the reactants.

The alkali metal hydroxide may include any alkali metal. Representative examples of alkali metals include sodium, potassium, lithium, cesium and rubidium. The preferred alkali metal hydroxide for economic reasons is sodium hydroxide.

The alkali metal carbonate may include any alkali metal. Representative examples of alkali metals include sodium, potassium, lithium, cesium and rubidium. The preferred alkali metal carbonate for economic reasons is sodium carbonate.

The aqueous solutions of the alkali metal hydroxide and alkali metal carbonate of this invention are made up of a ratio of from 1 equivalent hydroxide:1 equivalent carbonate to 4 equivalents hydroxide:1 equivalent carbonate. Thus, the equivalent ratio of hydroxide to carbonate is from 1:1–4:1. Preferably, this ratio is from 2:1–3:1. An equivalent is the amount that will neutralize 1 gram equivalent of hydrogen ion. At equivalent ratios below 1:1, the losses of acetylene are greater due to the generation of larger amounts of $CO_2$ by the larger carbonate content. At ratios above 4:1, the pH control is not satisfactory due to inability to maintain sufficient $CO_2$ in the system. With little or no carbonate present, even a small excess of formic acid over hydroxide will drive the pH below the desired range and thus substantially reduce the ethynylation rate. With little or no carbonate present, even a small excess of hydroxide over formate will drive the pH above the desired range and thus promote the formation of undesirable by-products and reduce the yield of butynediol.

The alkali metal hydroxide and alkali metal carbonate of the invention is critical. Use of an alkali metal hydroxide alone or an alkali metal carbonate alone will not give the beneficial results of the present process. For example, sodium hydroxide additions to control the pH in the present process at 5–8 in commercial facilities is not practical because even the smallest excess of NaOH will cause the pH to rise above 8. Therefore, pH control within 5–8 cannot be adequately maintained commercially.

Use of an alkali metal carbonate alone, for example, $Na_2CO_3$, results in formation of $CO_2$ in excess of that needed to facilitate pH control, and which must eventually be purged from the recycled acetylene. This purging results in substantial losses of acetylene. Additions of $Na_2CO_3$ alone to control the pH between 5–8 causes a substantially greater amount of $CO_2$ formation than the use of the present compositions.

The concentration of alkali metal hydroxide and alkali metal carbonate may vary rather widely. Generally, the concentration of alkali metal hydroxide will be from 0.5–10%, preferably 0.5–5%.

In the ethynylation process of this invention formaldehyde and acetylene are contacted in the presence of a copper acetylide catalyst in an agitated aqueous medium in a continuous reaction. The catalyst may be in a fixed bed or a slurry of particulate catalyst in the aqueous medium. Preferably, the catalyst is in the form of a slurry since backmixing which provides more homogeneous control of pH is readily achieved in this manner. In a slurry catalyst system the formaldehyde and acetylene are continuously fed into, and preferably below the surface of, the aqueous catalyst slurry in the reaction zone, and thoroughly mixed with the catalyst slurry by mechanical stirring, gas agitation, sonic waves or other means. The effluent is continuously withdrawn from the reaction zone, such as through filter elements immersed in the agitated catalyst slurry which separate the catalyst from the liquid effluent.

The catalyst used in the ethynylation reaction may be any copper acetylide. It may be supported or unsupported. Suitable supports include silica gel and activated carbon. The catalyst may be prepared by passing acetylene over a suitable copper compound such as cupric or cuprous chloride or the catalyst may be prepared in situ during the ethynylation reaction. The preferred ethynylation catalysts used in the process of this invention are the particulate catalysts described by Kirchner in U.S. Pat. No. 3,650,985 which is hereby incorporated by reference.

The amount of catalyst used in the ethynylation process is not critical, but is preferably such as to provide about 0.1–25% by weight of copper based on the total liquid medium. The reaction temperature is desirably maintained at about 60°–120° C., and preferably about 80°–100° C.

The formaldehyde concentration in the liquid medium in contact with the slurried catalyst during the course of the ethynylation reaction will be ordinarily about 0.5–20, and preferably about 2–15, weight percent under steady state conditions. The acetylene partial pressure may vary from subatmospheric to elevated pressures of about 20 atmospheres or higher. Preferably, the acetylene partial pressure is in the range of about 0.001–2 atmospheres. Advantageously, the acetylene partial pressure will be in the range of about 0.005–0.5 atmosphere per weight part of formaldehyde present in 100 parts of said medium, and preferably about 0.01–0.3 atmosphere per weight part of formaldehyde present in 100 parts of said medium. In the substantial absence of extraneous gas, the acetylene partial pressure may be taken as the absolute pressure less the vapor pressure of water at the reaction temperature. Crude acetylene may be used, but for safety reasons it should be substantially free of oxygen.

The effluent from the ethynylation reactor is heated to volatilize formaldehyde, propargyl alcohol and a portion of the water present. These volatile components are then condensed and combined with supplemental concentrated formaldehyde for recycle to the ethynylation reactor while purging any buildup of methanol at convenient intervals. The balance of the effluent is recovered as aqueous butynediol. It is in the reboiler of this recycle unit that the process of the invention eliminates a fouling problem that could occur when, for example, calcium carbonate is employed.

As previously indicated, the process of the invention also eliminates or reduces the fouling problems encountered when the butynediol product is used to make tetrahydrofuran. Particularly the process results in the elimination or reduction in the fouling in the recycle column and also the fouling of the Raney nickel catalyst used in the subsequent step of hydrogenating the butynediol.

In the process of the present invention the hydroxide and carbonate usage results in a reduction in the loss of acetylene due to venting or purging to remove $CO_2$ that is liberated when other pH control agents such as calcium carbonate or sodium bicarbonate are used. Thus, an increase in yield of acetylene to butynediol over that achieved with carbonate salt usage is attained by the present process.

BEST MODE

Formaldehyde and acetylene are contacted in the presence of a copper acetylide catalyst in an agitated aqueous medium in a continuous reaction at 80°–100° C. at a pH controlled at from 5–8 by the incremental addition of an aqueous solution of 0.5–5% of a mixture of an alkali metal hydroxide and an alkali metal carbonate at an equivalent ratio of from 1:1–4:1 of hydroxide to carbonate.

The following examples further illustrate the process of the present invention. All parts and percentages are by weight unless indicated otherwise.

EXAMPLES

Example 1

(Showing use of a mixture of 3 equivalents NaOH/1 equivalent $Na_2CO_3$ to control pH)

A jacketed 1-liter reactor was charged with 637 g of a mixture containing approximately 74 g of ethynylation catalyst and 77 g $CH_2O$ (the remaining 486 g consisted essentially of water and butynediol). The reactor and auxiliaries were purged first with $N_2$, then with $C_2H_2$ to establish an atmosphere in which $C_2H_2$ made up about 90% by volume of the noncondensable gases (the balance $N_2$, $CO_2$ and other inerts). The mixture was agitated by a magnetic stirrer and by recirculating gas through the reactor at a rate of about 400 ml/min. Acetylene was introduced to bring the pressure in the reactor to about 3.5 psig and hot water was circulated through the jacket to raise the temperature to about 90° C. Acetylene was fed on demand to maintain the 3.5 psig pressure. Formaldehyde (30.5% aqueous solution) was fed continuously to the reactor at a rate sufficient to maintain an average $CH_2O$ concentration of about 10%. A solution of 3.4% by weight NaOH and 1.5% by weight $Na_2CO_3$ (3 equivalents NaOH per equivalent of $Na_2CO_3$) in water was added incrementally to maintain pH 6.0–6.5. Product was withdrawn continuously through a sintered glass filter at a rate sufficient to maintain constant liquid level in the reactor. Acetylene and impurities were vented at a rate sufficient to maintain an acetylene concentration of 85–90% by volume of the noncondensable gases above the liquid. Maintaining pH required 3.7 milliequivalents of base (NaOH+$Na_2CO_3$) per equivalent of $CH_2O$ fed, and approximately 2.5% by volume of the acetylene fed was vented to maintain acetylene concentration. A summary of data is in the Table that follows the Examples.

Comparative Example A (Showing use of $Na_2CO_3$ alone to control pH)

A jacketed 1-liter reactor was charged with 642 g of a mixture containing about 74 g of ethynylation catalyst and 72 g $CH_2O$ (the remaining 496 g consisted essentially of water and butynediol). The reactor was started and operated as in Example 1, except that pH was controlled by incrementally adding a solution of 6.0% by weight $Na_2CO_3$ in water. Maintaining pH required 7.6 milliequivalents of base ($Na_2CO_3$) per equivalent of $CH_2O$ fed, and approximately 6.8% by volume of the acetylene fed was vented to maintain acetylene concentration. A summary of data is in the Table that follows the Examples.

Example 2

(Showing use of a mixture of 1 equivalent NaOH/1 equivalent $Na_2CO_3$)

A jacketed 1-liter reactor was charged with 670 g of a mixture containing about 78 g of ethynylation catalyst and 79 g $CH_2O$ (the remaining 513 g consisted essentially of water and butynediol). The reactor was started and operated as in Example 1, except that pH was controlled by incrementally adding a solution of 2.3% by weight NaOH and 3.0% by weight $Na_2CO_3$ (1 equivalent NaOH per 1 equivalent $Na_2CO_3$). Maintaining pH required 3.5 milliequivalents of base (NaOH+$Na_2CO_3$) per equivalent of $CH_2O$ fed, and about 2.3% by volume of the acetylene fed was vented to maintain acetylene concentration. A summary of data is in the Table that follows the Examples.

Comparative Example B (Showing use of NaOH alone to control pH)

A jacketed 750 ml reactor was charged with 400 g of a mixture containing about 46 g of ethynylation catalyst and about 43 g $CH_2O$ (the remaining 311 g consisted essentially of water and butynediol). The reactor was started and operated as in Example 1, except that pH was controlled by incrementally adding a solution of 5% by weight NaOH. Maintaining pH required 2.2 milliequivalents of NaOH per equivalent of $CH_2O$ fed. At about pH 6, each drop of NaOH solution abruptly increased the pH by 0.05–0.1 unit and at about pH 6.5, each drop of base abruptly increased the pH by 0.1–0.2 unit. About 4.3% by volume of the acetylene fed was vented to maintain acetylene concentration. A summary of data is in the Table that follows.

TABLE

| Example | Temperature, °C. Min | Avg | Max | pH Min | Max | % HCHO Min | Avg | Max | $C_2H_2$ Partial Pressure (Atm, Absolute)* Min | Avg | Max | % $CO_2$ by volume in Noncondensable Gases Vented Min | Avg | Max | meq Buffer(s)/ eq HCHO | $C_2H_2$ Vented/ $C_2H_2$ Fed |
|---|---|---|---|---|---|---|---|---|---|---|---|---|---|---|---|---|
| 1 | 89.7 | 90.0 | 90.2 | 6.20 | 6.56 | 10.8 | 13.4 | 14.5 | 0.32 | 0.43 | 0.47 | 1.5 | 4.1 | 6.9 | 3.1 | 0.025 |
| 2 | 89.7 | 90.1 | 90.1 | 6.08 | 6.48 | 7.5 | 8.7 | 10.3 | 0.32 | 0.44 | 0.47 | 2.1 | 5.7 | 8.7 | 3.5 | 0.023 |
| Com. A | 88.7 | 89.6 | 90.2 | 6.00 | 6.38 | 9.8 | 11.3 | 12.3 | 0.47 | 0.48 | 0.50 | 2.2 | 9.7 | 13.0 | 7.6 | 0.068 |
| Com. B | 90.1 | 90.2 | 90.2 | 6.01 | 6.63 | 8.9 | 9.7 | 10.4 | 0.43 | 0.46 | 0.48 | 0.2 | 1.4 | 1.8 | 2.2 | 0.043 |

*It is assumed that vapor pressure of condensable vapors equals that of water at the same temperature.

Butynediol is useful as an intermediate in the preparation of tetrahydrofuran.

Although the invention has been described and exemplified by way of specific embodiments, it is not intended that it be limited thereto. As will be apparent to those skilled in the art, numerous modifications and variations of these embodiments can be made without departing from the spirit of the invention or the scope of the following claims.

INDUSTRIAL APPLICABILITY

The present process enables one to control the pH of the reaction of formaldehyde and acetylene more uniformly than heretofore possible and while substantially reducing losses of acetylene that result from removal of $CO_2$ buildup in the reaction system. In the commercial production of 1,4-butanediol from such reactions maintaining the pH in the desired range can be more easily managed.

We claim:

1. In the process for the production of butynediol by contacting acetylene and formaldehyde in the presence of a particulate copper acetylide catalyst in an agitated aqueous medium in a continuous reaction at 60°–120° C., the improvement wherein the pH of the reaction mixture is maintained at from 5–8 by the incremental or continuous addition of an aqueous solution of an alkali metal hydroxide and an alkali metal carbonate at equivalent ratios of alkali metal hydroxide to alkali metal carbonate of 1:1–4:1.

2. The process of claim 1 wherein the ratio is 2:1–3:1.

3. The process of claim 1 wherein the alkali metal hydroxide is sodium hydroxide.

4. The process of claim 1 wherein the alkali metal carbonate is sodium carbonate.

5. The process of claim 4 wherein the alkali metal hydroxide is sodium hydroxide.

6. The process of claim 1 in which the pH is in the range of 6–6.5.

7. The process of claim 6 wherein the ratio is 2:1–3:1.

8. The process of claim 6 wherein the alkali metal hydroxide is sodium hydroxide.

9. The process of claim 6 wherein the alkali metal carbonate is sodium carbonate.

10. The process of claim 9 wherein the alkali metal hydroxide is sodium hydroxide.

11. The process of claim 1 wherein the aqueous solution is a mixture of alkali metal carbonate and alkali metal hydroxide.

12. The process of claim 11 wherein the ratio is 2:1–3:1.

13. The process of claim 11 wherein the alkali metal hydroxide is sodium hydroxide and the alkali metal carbonate is sodium carbonate.

14. The process of claim 11 wherein the pH is 6–6.5.

* * * * *